United States Patent [19]

Habal et al.

[11] 4,313,232
[45] Feb. 2, 1982

[54] AN ELASTOMERIC MESH HINGE PRIMARILY FOR REPLACEMENT OF THE FINGER JOINTS

[76] Inventors: Mutaz B. Habal, 12901 N. 30th St., Box 16, Tampa, Fla. 33612; Donald L. Leake, 2 Crest Rd., West, Rollings Hills, Calif. 90274

[21] Appl. No.: 196,155

[22] Filed: Oct. 10, 1980

Related U.S. Application Data

[63] Continuation of Ser. No. 2,545, Jan. 10, 1979, abandoned.

[51] Int. Cl.³ .............................................. A61F 1/03
[52] U.S. Cl. ..................................... 3/1.91; 128/92 C
[58] Field of Search ............................... 3/1, 1.9, 1.91

[56] References Cited

U.S. PATENT DOCUMENTS

| | | | |
|---|---|---|---|
| 3,462,765 | 8/1969 | Swanson | 3/1.91 |
| 3,593,342 | 7/1971 | Niebauer et al. | 3/1.91 |
| 3,818,513 | 6/1974 | Pillet | 3/1.91 |
| 3,824,631 | 7/1974 | Burstein et al. | 3/1.91 |
| 3,875,594 | 4/1975 | Swanson | 3/1.91 |
| 3,879,767 | 4/1975 | Stubstad | 3/1.91 |
| 3,882,551 | 5/1975 | Helmer et al. | 3/1 |
| 3,886,600 | 6/1975 | Kahn et al. | 3/1.91 |
| 3,986,212 | 10/1976 | Saver | 3/1.91 |
| 3,990,116 | 11/1976 | Fixel et al. | 3/1.91 |

OTHER PUBLICATIONS

Boretos, John W.; *Concise Guide to Biomedical Polymers*, "Biomedical Polymers", pp. 10, 11; 1973.

*Primary Examiner*—Clifford D. Crowder
*Attorney, Agent, or Firm*—Duckworth, Allen, Dyer & Pettis

[57] ABSTRACT

A non-metallic joint prosthesis having a plurality of pores penetrating the thickness of the non-metallic material and primarily intended for use for replacing damaged joints in humans. The prosthetic blank is substantially elongate in configuration, and the opposite end portions are tapered so as to define a relatively wider central segment. The entire blank is reinforced by impregnation with a biocompatible elastomer, and then the tapered opposite end portions are provided with additional quantities of the reinforcing material to facilitate their attachment to the bone structures. Also disclosed and claimed is a method for fabricating the prosthetic blank as well as a method for repairing damaged joints using the prosthesis.

2 Claims, 4 Drawing Figures

AN ELASTOMERIC MESH HINGE PRIMARILY FOR REPLACEMENT OF THE FINGER JOINTS

This is a continuation of application Ser. No. 002,545, filed Jan. 10, 1979, now abandoned.

BACKGROUND OF THE INVENTION

1. Field of the Invention

The present invention relates to a non-metallic joint prosthesis of the type primarily intended for use in replacing damaged joints between long bones of the human body. Also disclosed and claimed are the method for fabricating the prosthesis and a method for repairing damaged joints using the prosthesis.

2. Description of the Prior Art

During the past decade the ability to treat patients with joint problems has become more evident. Due primarily to the pioneer work of Charnly in England, one of the major weightbearing joints in the body, the hip joint, has become easily replaceable with artificial components. In similar fashion, small joints in the hands, requiring delicate and fine motor control, have also become amenable to replacement. The patients most commonly requiring this type of treatment are patients with rheumatoid arthritis and other forms of arthritis. Traumatic disruption of the joints plays a minor part where the placement of a joint prosthesis is called for. It is estimated that over 25,000 such joint substitutes have been placed each year.

Under state-of-the-art techniques, silicone rubber joints are most commonly utilized. There are different variants of these joints, but in principle they are all quite similar. While the silicone rubber joints are clearly acceptable, there are two factors that preclude their being the ideal, or optimal, joint prosthesis.

The first major difficulty is identified as implant fracture which simply results from "wear and tear." The silicone rubber cannot withstand the repeated motion experienced in joints, so it fractures. This results in a major complication requiring a substitution of the joint and unwarranted replacement of parts, with major hospitalization, anesthetic and other ancillary expenses. The second major problem is related to the inability of the silicone to be incorporated in the hard or soft tissue that surrounds the silicon rubber prosthesis. Therefore, with continuous joint movement, the ends of the prosthesis become loose, and there is widening and destruction of the bone with which the prosthesis is in contact.

Another type of joint prosthesis currently available is known as the Mayo clinic implant. The Mayo clinic implant comprises a metal ball and socket structure. As with the silicon rubber prosthesis, this implant also exhibits certain undesirable characteristics. Of particular importance is the inapplicability of a Mayo clinic implant as for replacing finger joints. The implant does not provide sufficient lateral stability for such joints, and will not stay in place under skin such as that surrounding finger joints.

It is therefore apparent there is a great need in the art for a joint prosthesis suitable for use in the human body and decreasing, if not eliminating, the undesirable and deleterious effects associated with state-of-the-art prosthetic joints. Of course, such a joint prosthesis must be fabricated from a material suitable for implanting within the human body. With particular regard to the rising cost of medical treatment and care throughout the world, it is furthermore desirable that the joint prosthesis be relatively easy to manufacture and to implant. For similar reasons, as well as for the well-being of the patient, such a joint prosthesis should have an anticipated lifetime coincident to that of the patient.

SUMMARY OF THE INVENTION

The present invention comprises a non-metallic joint prosthesis primarily intended for use in replacing damaged joints in the human body as well as methods for fabricating and for implanting the prosthesis. For purposes of definition, the phrase "non-metallic material" is meant to convey a biocompatible cloth mesh such as, for example, Dacron or nylon mesh reinforced with a suitable elastomer such as polyether urethane, as described in U.S. Pat. No. 3,849,805, to Leake et al. It is, of course, to be understood that other plastic or non-metallic materials may be utilized within the scope of this invention.

It is furthermore to be understood that while the remainder of this summary as well as the ensuing detailed description will be given with regard to a joint prosthesis for finger joints, the invention is not limited to that application. It is intended that the joint prosthesis and methods of this invention may be utilized for joint replacement between adjacent long bones of both humans and animals.

A standard elongate prosthetic blank is prepared by tapering opposite end sections of the blank so as to define a relatively wider central segment. The entire blank is then impregnated with a reinforcing means comprising a polyether urethane elastomer primarily so as to provide lateral stability to the finished prosthesis. The opposite end portions are then rolled axially about the longitudinal dimension of the blank and additional reinforcing means is applied to each end portion. Final fitting of the prosthesis can be made at the operating table using only scissors for trimming and shaping. This allows the surgeon great flexability in adapting a suitable prosthesis to the patient simply and effectively.

With specific regard to implantation of the prosthesis between adjacent phalangeal bones, the surgeon first removes the damaged joint. He then reams a longitudinal passage in each of the phalangeal bone ends and inserts the reinforced end portions of the prosthesis in the passageways. Dependent upon the particular needs of the operation, these opposite end portions may be fixed in place as by bone chips or segments that have been removed from the destroyed articular surfaces. This effectively "locks" the prosthesis in place. It should also be noted that because the prosthesis has a plurality of pores penetrating the thickness of the opposite end portions of the non-metallic material, bone will actually grow into and through the prosthesis, fixing the joint in place well inside the bone structure. In corresponding fashion, soft tissue will grow on the more mobile wider central segment. As a further aid to understanding this preferred embodiment for the joint prosthesis, its method of fabrication, and its method of implantation it should be noted that the basic elongate prosthetic blank will be about 5–6 mm in width.

The invention accordingly comprises an article of manufacture possessing the features, properties and the relation of elements which will be exemplified in the article hereinafter described, as well as the several steps in the relation of one or more of such steps with respect to each of the others, which will be exemplified in the method hereinafter disclosed, and the scope of the invention will be indicated in the claims.

BRIEF DESCRIPTION OF THE DRAWINGS

For a fuller understanding of the nature and objects of the invention, reference should be had to the following detailed description taken in conjunction with the accompanying drawings, in which.

Similar reference characters refer to similar parts throughout the several views of the drawings.

DETAILED DESCRIPTION

Figure 1:
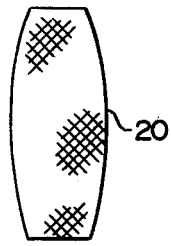
FIG. 1 is a plan view of the elongate prosthetic blank.

The present invention comprises a non-metallic joint prosthesis, generally indicated as 10, formed from a non-metallic material including a plurality of pores penetrating the thickness thereof. Attention is invited to the view of FIG. 4 wherein the implantation of three such prostheses, 10, 10a and 10b, is shown between adjacent long bone structures of a hand. Joint prosthesis 10 is implanted in interconnecting relation between metacarpal 12 and proximal phalanx 14. Prosthesis 10a interconnects proximal phalanx 14 and middle phalanx 16, and prosthesis 10b is similarly disposed between middle phalanx 16 and distal phalanx 18. While a more specific description of prosthesis 10 as well as its method of fabrication and implantation will be given below, attention is first invited to the views of FIGS. 1 and 2.

FIG. 1 depicts a rough blank 20 from which a prosthesis 10 will be formed. Rough blank 20 is substantially elongate in configuration, and is formed from a Dacron or nylon mesh material. A plurality of pores extend through the thickness of blank 20 and those pores are preferably of a size no greater than 0.5 microns. Due to their small size it is not feasible to illustrate the pores in the views of the drawings, but the cross-hatch shading is intended to be representative thereof. The relatively small size of the pores effectively prevents the formation of blood vessels therethrough, while at the same time providing a suitable surface for the formation of interconnecting bone tissue and soft tissue around the implanted prosthesis 10. The pores may be omitted in central segment 28.

Figure 2:
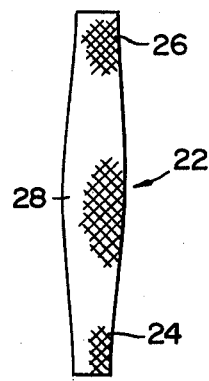
FIG. 2 is a plane view of the blank of FIG. 1 wherein opposite end portions are tapered so as to define a relatively wider central segment.

The view of FIG. 2 illustrates a finished blank generally indicated as 22. As shown therein, opposite end portions 24 and 26 have been tapered so as to define a relatively wider central segment 28. The entire substance of finished blank 22, including end portions 24 and 26 and central segment 28, are impregnated with a reinforcing means such as, for example, a polyether urethane elastomer. Not only does this reinforce the body of finished blank 22, but also it provides for lateral stability so that central segment 28 will flex along a single plane. Attention is now invited to the view of FIG. 3 wherein prosthesis 10 is shown in its final form, ready for surgical implantation.

Figure 3:
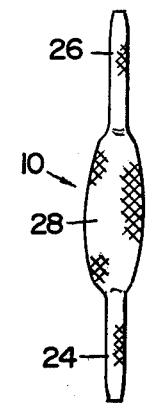
FIG. 3 is a plan view of the finished joint prosthesis ready for implantation.
Figure 4:
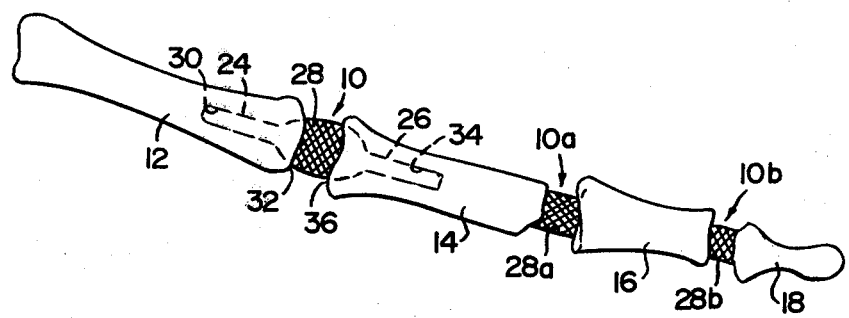
FIG. 4 is a plan view, with interior detailed shown in broken lines, showing implantation of three joints prostheses between metacarpal and phalangeal bones of a human.

As clearly seen in the view of FIG. 3, and as shown in the broken line portion of FIG. 4, opposite end portions 24 and 26 of prosthesis 10 have been rolled axially along the longitudinal dimension of finished blank 22 so as to facilitate surgical implantation. For the primary purpose of further reinforcing prosthesis 10, opposite end portions 24 and 26 are furthermore provided with an additional quantity of the reinforcing means described above. Central segment 28 does not receive any such additional reinforcing means so that it is free to flex as the prosthetic joint.

Turning now to the view of FIG. 4, the method and corresponding structure for surgically implanting prosthesis 10 can be seen. First, the surgeon removes the damaged joint such as would have existed between metacarpal bone 12 and proximal phalanx bone 14. The surgeon next reams longitudinal passages in the adjoining bones between which prosthesis 10 is to be implanted. In the example shown in FIG. 4, a longitudinal passage 30 is reamed from end 32 of the metacarpal bone 12. A corresponding longitudinal passage 34 is similarly reemed from end 36 of the proximal phalanx 14. End portion 24 of prosthesis 10 is inserted into passage 30, and the other end portion 26 is inserted into passage 34. At this point it should be noted that dependent upon the needs of the particular patient, prosthesis 10 can be trimmed by the surgeon in the operating room so as to insure a proper fit for prosthesis 10. Then, once the implantation has been made as shown in FIG. 4, opposite end portions 24 and 26 may be fixed in place as by bone chips or segments that have been removed from the destroyed articular surfaces. Again dependent upon the particular circumstances of the operation and the patient, such mechanical "locking" or "fixing" of prosthesis 10 may not actually be required. As previously stated, the nature of the non-metallic material from which prosthesis 10 is formed is such that bone will actually grow through end portions 30 and 34. This, then, leaves central segment 28 free to flex along a single plane as an interconnecting, hinged joint between metacarpal bone 12 and proximal phalanx 14. Corresponding hinge portions of prosthesis 10a and prosthesis 10b are similarly illustrated in the view of FIG. 4.

While the above detailed description has been given with specific regard to a preferred embodiment of the present invention as a joint prosthesis between adjacent bones and humans hand it is to be understood that the scope of the invention is not limited thereto. Furthermore, while the non-metallic material has been defined as comprising Dacron or nylon the substitution of similar, biologically-inert substances therefor is deemed to fall within the scope of this invention.

It will thus be seen that the objects setforth above, among those made apparent from the preceding description, are efficiently attained, and since certain changes may be made in the above article or in carrying out the method described without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for preparing a joint prosthesis of the type primarily intended for use in repairing joints between adjacent long bones of a human, said method comprising the steps of:
  a. trimming opposite end portions of a biocompatible cloth mesh so as to provide an elongate prosthetic blank wherein said opposite end portions extend from a relatively wider central segment;
  b. impregnating said blank with a reinforcing material;
  c. rolling said end portions axially about the longitudinal dimension of said blank; and
  d. applying sufficient additional quantities of said reinforcing material to said rolled end portions so as to eliminate substantially flexing of said opposite end portions with respect to the longitudinal dimension of said blank, whereby said opposite end portions are suitable for attachment in interconnecting relation between adjacent bone structure and said central segment will flex along a single plane.

2. A method as in claim 1 wherein said reinforcing material comprises a polyether urethane elastomer.

* * * * *